United States Patent [19]

Pasqualucci et al.

[11] Patent Number: 4,913,703
[45] Date of Patent: Apr. 3, 1990

[54] SAFETY INTERLOCK SYSTEM FOR MEDICAL FLUID PUMPS

[75] Inventors: Joseph Pasqualucci; Frederick F. Schweitzer, both of Watertown, N.Y.

[73] Assignee: Sherwood Medical Company, St. Louis, Mo.

[21] Appl. No.: 103,432

[22] Filed: Sep. 30, 1987

[51] Int. Cl.$^4$ .............................................. A61M 1/00
[52] U.S. Cl. .................................... 604/153; 604/151
[58] Field of Search ..................... 604/50, 67, 151–153, 604/254; 417/63, 360, 474–477; 324/207, 208, 226, 228, 234, 235, 251, 252, 260, 262; 128/DIG. 12, DIG. 13; 73/863.33

[56] References Cited

U.S. PATENT DOCUMENTS

| 3,739,943 | 6/1973 | Wilhelmson et al. |
| 4,187,057 | 2/1980 | Xanthopoulos |
| 4,211,519 | 7/1980 | Hogan |
| 4,221,543 | 9/1980 | Cosentino et al. |
| 4,363,609 | 12/1982 | Cosentino et al. |
| 4,373,525 | 2/1983 | Kobayashi |
| 4,460,358 | 7/1984 | Somerville et al. |
| 4,493,706 | 1/1985 | Borsanyi et al. |
| 4,515,535 | 5/1985 | D'Silva |
| 4,551,134 | 11/1985 | Slavik et al. |
| 4,585,399 | 4/1986 | Baier |
| 4,599,055 | 7/1986 | Dykstra ............................ 417/477 |
| 4,601,211 | 7/1986 | Whistler ........................ 73/863.33 |
| 4,652,262 | 3/1987 | Veracchi ............................ 604/250 |

Primary Examiner—Michael H. Thaler
Assistant Examiner—W. Lewis
Attorney, Agent, or Firm—Andrew J. Beck; Montgomery W. Smith; Richard D. Allison

[57] ABSTRACT

A medical fluid delivery set is provided with a magnetic field source in the region of its mounting to a fluid flow control apparatus. The flow control apparatus includes a magnetic field sensitive switching component which detects the proper placement of the delivery set on the flow control apparatus and prevents operation of the fluid delivery system unless a set is in proper position.

9 Claims, 4 Drawing Sheets

SAFETY INTERLOCK SYSTEM FOR MEDICAL FLUID PUMPS

BACKGROUND OF THE INVENTION

This invention relates to fluid delivery systems for providing perenteral nutrition, enteral nutrition or other fluids to patients who require infusion of fluids. The invention is particularly related to improvements in such systems which use a disposable fluid delivery set in conjunction with a fluid flow control unit, such as a pump motor set, for supplying such fluids to a patient at a controlled delivery rate.

The assignee of the present invention presently markets an enteral delivery system under the trade name "Kangaroo". The system includes a fluid delivery motor set and a disposable fluid delivery set, which includes a fluid tube, a drip chamber which is arranged to be mounted to recess on the motor set, a mounting member, also arranged to be mounted to a recess on the motor set, an outlet tube connected to the mounting member and a pump tube which connects the drip chamber to the mounting member and engages a motor driven rotor on the motor set to form a peristaltic pump.

In the Kangaroo enteral delivery system the engagement of the pump tube to the rotor controls the flow of fluid to the patient according to the speed of the rotor. In the event the delivery set is not properly mounted to the motor set and the pump tube is not firmly engaged with the rotor, an excess flow of fluid through the set can occur under force of gravity. Improper mounting of the drip chamber is unlikely because of the mechanical configuration of that component and its corresponding recess. Improper placement of the mounting member, e.g. below, above or outside of the receiving recess, is possible if the delivery set is installed on the motor set by an operator who has not received proper instruction in the operation of the system. Instances of such improper installation have been reported.

It is an object of the present invention to provide an interlock system which prevents operation of a fluid delivery system unless the delivery set is properly placed and installed on the flow control unit.

SUMMARY OF THE INVENTION

The present invention is applicable in a medical fluid delivery system which includes a fluid delivery set arranged to be mounted on a corresponding fluid delivery flow control apparatus. According to the invention there is provided a method for preventing improper system operation which comprises the steps of providing a switching component on the flow control apparatus which has a first electrical state when the delivery set is properly mounted to the flow control apparatus and a second electrical state when the delivery set is not properly mounted to the flow control apparatus. According to the invention operation of the flow control apparatus is enabled in response to the first electrical state and disabled in response to the second electrical state. The second electrical state will also cause an alarm to be activated when operation is attempted.

According to the invention there is provided a fluid flow control apparatus which is arranged to receive a corresponding fluid delivery set. The fluid flow control apparatus is provided with a switching component responsive to proper mounting of a fluid delivery set and is provided with control means responsive to the switching component for permitting operation of the flow control apparatus only when the switching component detects proper mounting of the fluid delivery set. Preferably the switching component is a magnetic field sensitive component.

In accordance with the invention there is provided a disposable medical fluid delivery set arranged to be mounted to a fluid flow control apparatus which is arranged for operating with portions of the set for controlling the rate of fluid delivery. According to the invention there is provided an improvement comprising a magnetic field source on the fluid delivery set, the source being arranged in a position on the set which corresponds to a magnetic field sensitive component on the control apparatus. In a preferred embodiment the fluid delivery set includes at least one mounting member arranged for attachment to a corresponding receiving member on the control apparatus and the magnetic field source is mounted on the mounting member.

For a better understanding of the present invention, together with other and further objects, reference is made to the following description, taken in conjunction with the accompanying drawings, and its scope will be pointed out in the appended claims.

DESCRIPTION OF THE INVENTION

Figure 1:
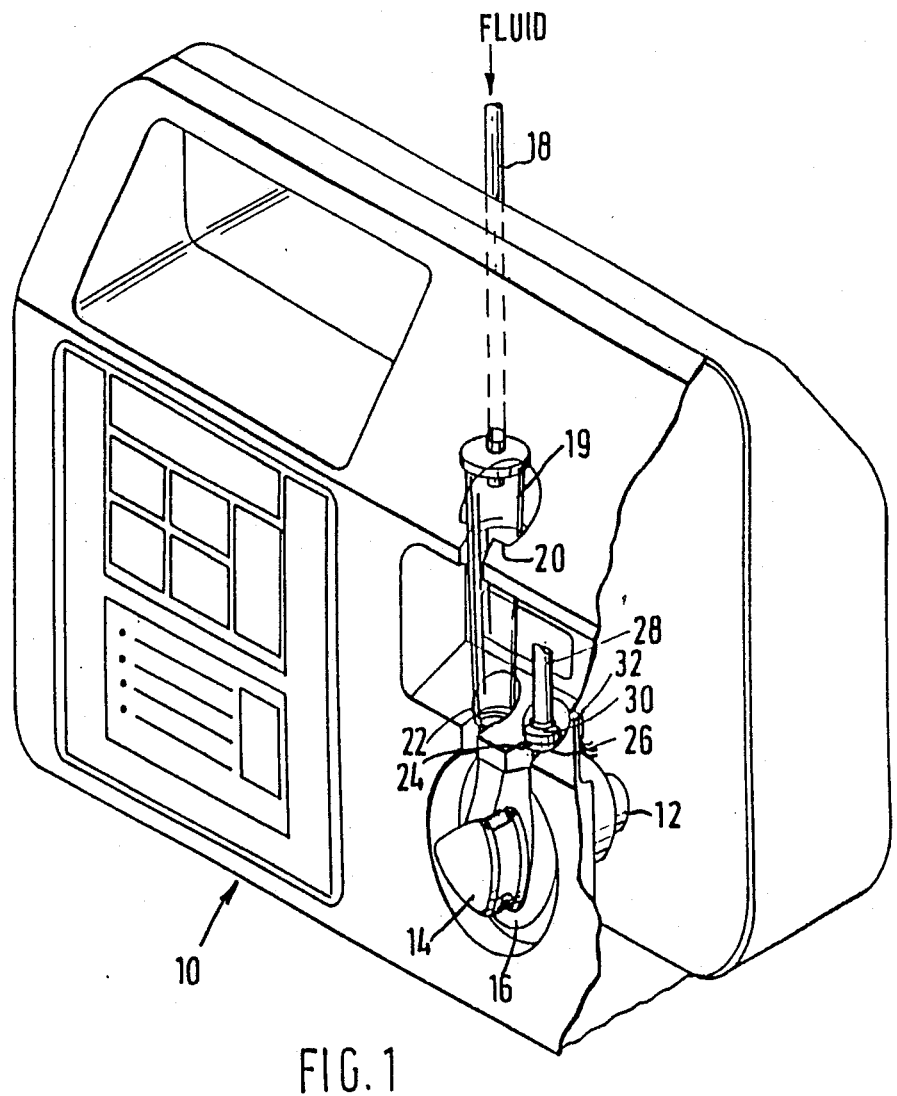
FIG. 1 is perspective view of a medical fluid delivery system incorporating the present invention.

FIG. 1 is a perspective view of an enteral fluid delivery system incorporating the present invention. The system includes a motor set 10 upon which is mounted a disposable delivery set which includes inlet tube 18 which is connected to a source of fluid, drip chamber 19 which is connected to receive fluid from tube 18 and is mounted in recesses 20 and 22 on motor set 10. The delivery set also includes a pump tube 16 which is connected to the bottom of drip chamber 19 and which surrounds a pump rotor 14 on motor set 10 to form a peristaltic pump. The delivery set also includes a circular mounting member 24 which is received in mounting recess 26 which connects pump tube 16 to outlet tube 28. Rotor 14 on motor set 10 is driven by motor 12 and rotates at various speeds to control the rate of delivery of fluid, such as enteral nutrition fluid, to a patient.

Those familiar with the art will recognize that similar delivery sets and motor sets are used in connection with delivery of other medical fluids, such as intravenous i.e.

perenteral fluids, or blood. In some systems rather than provide a motor driven pump, as the motor set 10 of FIG. 1, there is provided a flow control apparatus which controls the flow of fluid by gravity, for example by exerting a valve-like force on a portion of the fluid delivery set.

The present invention is concerned with assuring proper placement of the fluid delivery set onto the motor set or other flow control apparatus, and in particular with the proper placement of the pump tube 16 around the rotor 14 to form a peristaltic pump which provides accurate and controlled delivery rates.

Figure 3A:
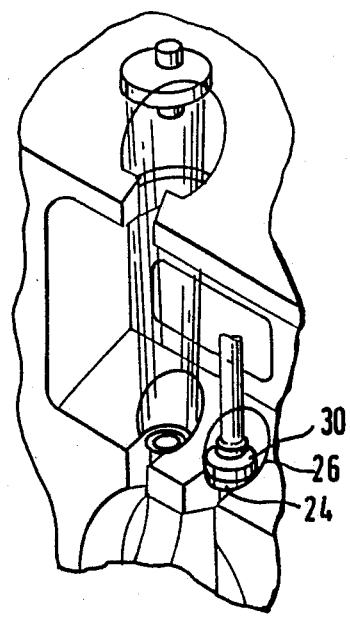
FIGS. 3A, 3B, 3C and 3D are detailed illustrations of a portion of the FIG. 1 system illustrating correct and incorrect positioning of a fluid delivery set.
Figure 3B:
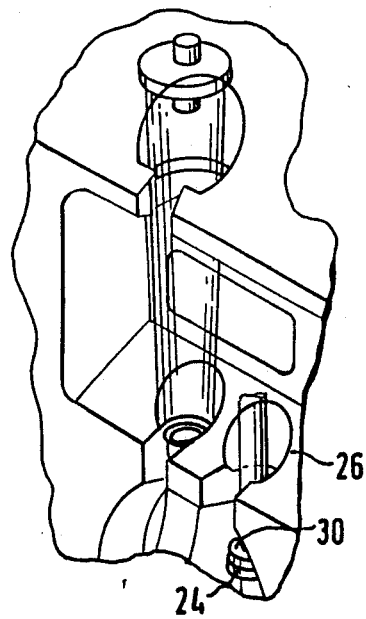
Figure 3C:
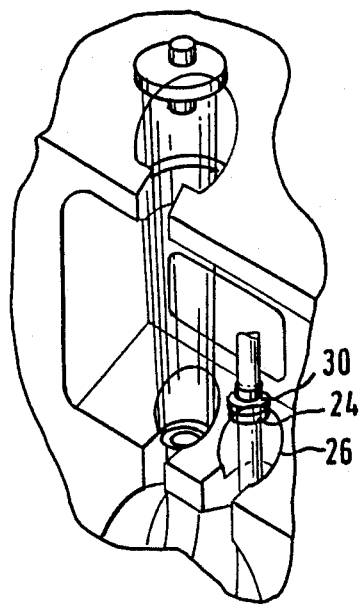
Figure 3D:
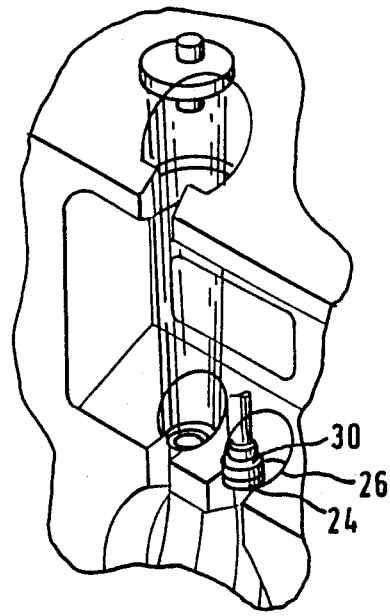

Pump tube 16 is mounted to drip chamber 22 at its inlet end and mounted to mounting member 24 at its outlet end. As illustrated in FIG. 1, drip chamber 19 is received in recesses 20 and 22 on motor set 10 and mounting member 24 is received in recess 26. When properly mounted pump tube 16, which is typically silicone tubing is tightly stretched around rotor 14 so that the points of rotor contact on tube 16 close the passage of fluid. Referring to FIG. 3 there is shown in FIG. 3A the correct arrangement of the drip chamber and mounting member in the recesses on motor set 10. As shown in FIG. 3A mounting member 24 should be fully received into recess 26. It has come to the inventors' attention that in some cases the mounting member 24 may be improperly installed by inexperienced personnel so that mounting member 24 is seated below recess 26 as shown in FIG. 3B. This arrangement can be hazardous to a patient because of excess and uncontrolled flow of fluid through the delivery set under force of gravity, whereby fluid is delivered at a higher rate than properly specified. Another improper mounting of the delivery set is illustrated in FIG. 3C, wherein mounting member 24 is caught on the lip of recess 26 and not properly seated in the recess itself. Another improper mounting is shown in FIG. 3D wherein mounting member 24 is not placed completely back into recess 26, but seats on the outer edge thereof.

In accordance with the present invention an arrangement is provided for detecting the proper placement of mounting member 24 in recess 26. Improper placement of drip chamber 19 is unlikely since it must engage both recess 20 and recess 22.

Figure 2:
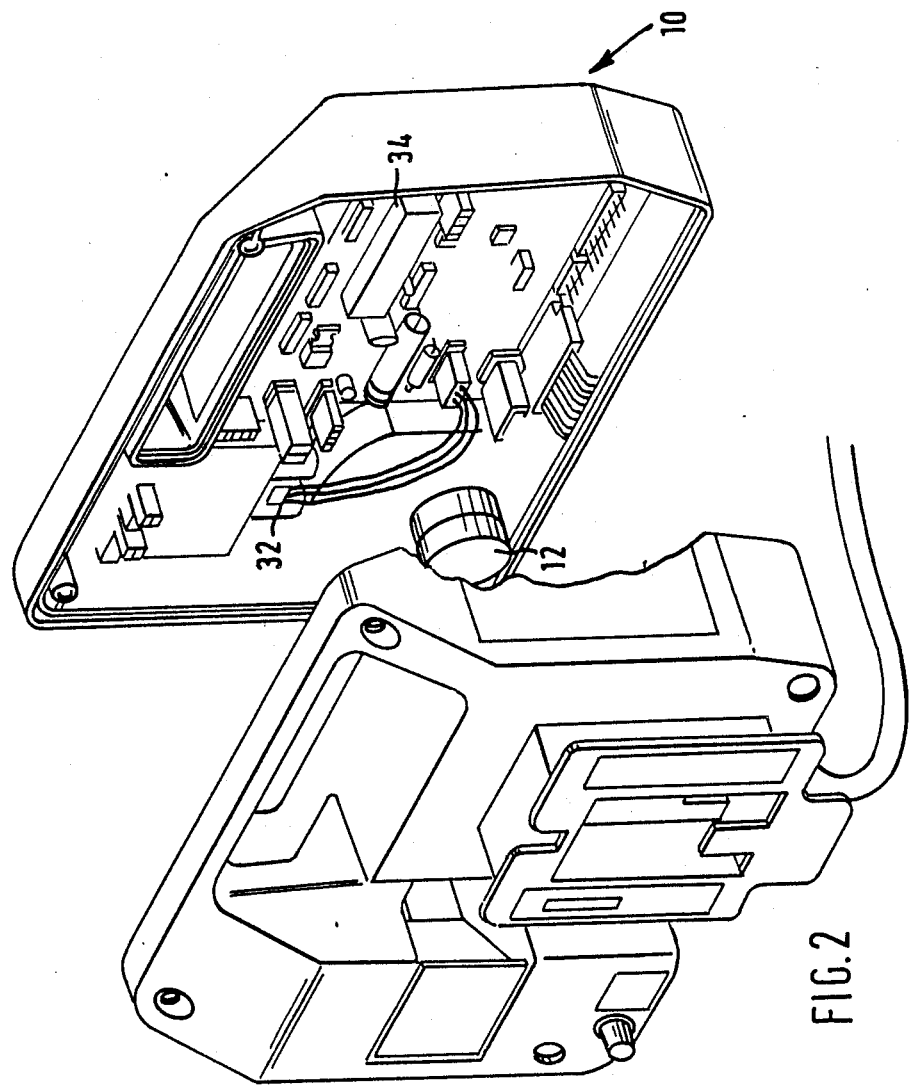
FIG. 2 is a perspective view of the interior of the medical fluid delivery system of FIG. 1.

In order to detect the proper placement of mounting member 24 in recess 26 there is provided a magnetic field source 30 which is a toroidal shaped piece added to mounting member 24 and surrounding the fluid passage thereof. A magnetic field detector 32 is provided within the motor set 10 and arranged to detect the magnetic field from magnetic field source 30 when mounting member 24 is properly received into recess 26. FIGS. 1 and 2 show generally the internal arrangement of motor set 10 indicating the placement of magnetic field detector 32 against the inside wall of the motor set adjacent recess 26.

Figure 4:
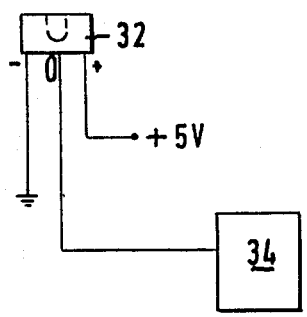
FIG. 4 is a schematic diagram illustrating the electrical connection of a switching component in the fluid delivery system of FIG. 1.

Magnetic field detector 32 is preferably a magneto resistive switching element, such as part No. SS21PE, available from Microswitch of Freeport, Ill. When connected as shown in FIG. 4 this part provides an output of plus 5 volts when not in the presence of a magnetic field and zero volts when in the presence of either polarity of magnetic field. The zero or plus 5 volt output signal of switching element 32 is connected to microprocessor 34 as a digital input signal to cause the motor set 10 to provide an error signal if an operator attempts to operate the motor set with an improperly placed delivery set. The error signal prevents operation of the motor set and preferably causes an alarm signal to be provided.

Figures 5, 6:
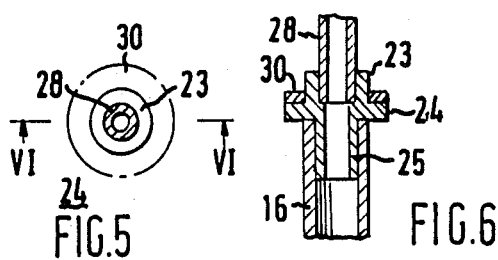
FIG. 5 is a top view of a mounting member in accordance with the present invention.
FIG. 6 is a cross-sectional view of a mounting member taken along the lines illustrated in FIG. 5.

FIG. 5 is a top view of mounting member 24 which is circular in cross-section and includes a central passage for fluids. A magnetic source 30 which is toroidal in shape is attached directly to the shoulder of mounting member 24 as shown in the cross-sectional view of FIG. 6. Magnetic source 30 surrounds an upwardly projecting tube receiving member 23 which connects to outlet tube 28. Mounting member 24 also includes a downwardly extending tube engaging member 25 which receives peristaltic pump tube 16. As an alternate to providing a separate magnetic field source 30, mounting member 24 can be formed entirely from magnetic material.

Figure 7:
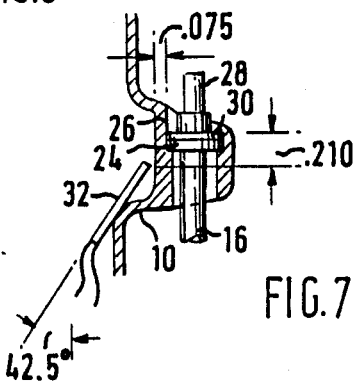
FIG. 7 is a cross-sectional view of the FIG. 1 fluid delivery system showing details of the components of the present invention.
Figure 8:
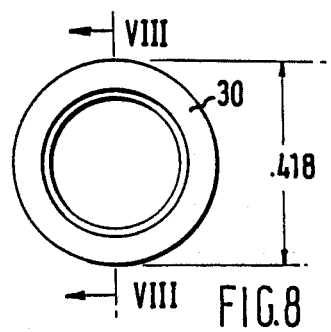
FIG. 8 is plan view of a magnetic field source used in the fluid delivery system of FIG. 1.
Figure 9:
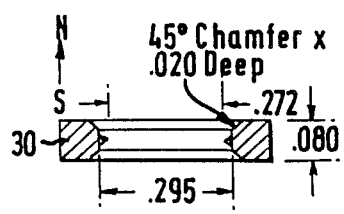
FIG. 9 is a cross-sectional view of a magnetic field source taken along the lines illustrated in FIG. 8.

FIG. 7 shows the details of one arrangement for detecting the presence of the magnetic element 30 surrounding mounting member 24. The magnetic sensitive switching component 32 is arranged on the inside wall of the motor set 10 with its magneto sensitive end pointing at an angle of 42.5° toward the magnetic field source 30 mounted on mounting member 24. The end of magnetic sensitive switching element 32 is vertically spaced 0.210 inches from the top of magnetic field source 30 and is horizontally spaced 0.075 inches from the outside diameter of magnetic field source 30. Details of magnetic field source 30 showing mechanical dimensions are ilustrated in FIGS. 8 and 9.

While it is believed that a wide variety of magnetic materials are suitable for the magnetic field source, the inventors have found that a material composed of 88% stronium ferrite and 12% #6 nylon to be a suitable material. This material is available from Tengan of Ostsego, Mich. the material is magnetized in the axial direction to a magnetic strength of 400 to 500 gauss at the surface edge.

Those skilled in the art will recognize that while the invention has been described with reference to application on an enteral delivery system, the present invention is likewise useable in connection with detecting the proper placement of a disposable delivery set on other medical fluid delivery systems, such as intravenous pumps or blood infusion pumps.

While the present invention has been described with respect to an embodiment which uses a magnetic field source on the disposable delivery set and a magnetic field sensitive swithing element on the motor set, those skilled in the art will recognize that other arrangements for detecting the presence of and proper placement of a mounting member on the motor set are possible, including arrangements of mechanical micro-switches on a pump motor set and switch activating devices on the disposable delivery set.

While there has been described what is believed to be the preferred embodiment of the invention, those skilled in the art will recognize that other and further modifications may be made thereto without departing from the spirit of the invention, and it is intended to claim all such changes and modifications as fall within the true scope of the invention.

We claim:

1. A medical fluid delivery system comprising;
   a peristaltic pump and a corresponding fluid delivery set operatively mountable on said peristaltic pump,
   a control means on said peristaltic pump for enabling operation of said peristaltic pump, said control means including a means for detecting a predetermined alignment of at least a portion of said fluid delivery set on said peristaltic pump, said control means enabling the operation of said peristaltic pump in response to the detection of said at least a portion of said fluid delivery set in the predetermined alignment on said peristaltic pump by said means for detecting, said fluid delivery set including a magnetic field source mounted in a predetermined position on said fluid delivery set, and said control means further including a magnetic field sensitive sensor located on said peristaltic pump for detecting said magnetic field source on said fluid delivery set.

2. The medical fluid delivery system of claim 1, wherein said magnetic field source is located on said fluid delivery set in a predetermined position for detection by said magnetic field sensitive sensor on said peristaltic pump when at least a portion of said fluid delivery set is in a predetermined longitudinal alignment on said peristaltic pump to allow fluid delivery by said peristaltic pump and wherein said magnetic field sensitive sensor does not detect said magnetic field source when at least a portion of said fluid delivery set is not in predetermined longitudinal alignment on said peristaltic pump.

3. The medical fluid delivery system of claim 2, wherein an alarm means is located on said peristaltic pump in operative communication with said switching component to activate said alarm means when at least a portion of said fluid delivery is not in predetermined longitudinal alignment on said peristaltic pump.

4. A fluid delivery apparatus for the delivery of a medical fluid to a patient, comprising
   a peristaltic pump having first and second receivers and a rotor thereon for controlling the rate of fluid delivery to a patient,
   a fluid delivery set including a fluid reservoir section, a fluid delivery section adapted to deliver fluid to a patient and a flexible tube section adapted to be placed in operative connection with said rotor on said pump and first and second mounting members wherein said second mounting member includes a magnetic field source thereon and said first and second mounting members are arranged in a predetermined configuration on said delivery set such that when said flexible tube section is aligned about said rotor, said first and second mounting members are insertable into said first and second receivers, and
   a switch means on said pump for detecting the insertion of said magnetic field source on said second mounting member into said second receiver and wherein said switch means enables said pump to rotate said rotor to deliver fluid to a patient when said second mounting member is detected in said second receiver.

5. A medical fluid delivery system for delivering medical fluid to a patient comprising
   a fluid delivery set having a fluid reservoir section, a drip chamber in fluid communication with the fluid reservoir section, a flexible tubing section adapted to be mounted in a predetermined configuration on a fluid delivery apparatus, a mounting member having a magnetic field source thereon and an elongate tubing section adapted to be placed in fluid communication with a patient,
   a peristaltic pump having a rotary member and first and second receiving members thereon wherein said drip chamber is mountable on said first receiving member and said mounting member is mountable on said second receiving member,
   a switch means on said peristaltic pump for enabling the operation of said rotary member in a first state and disabling operation of said rotary member in a second state,
   said drip chamber and mounting member being arranged in a predetermined configuration on said fluid delivery set adjacent to said flexible tubing section such that when said flexible tubing section is aligned about said rotor in a predetermined configuration and said drip chamber is inserted into said first receiving member and said mounting member is inserted into said second receiving member, said flexible tubing section is aligned about said rotary member in an operative contacting relation with said rotary member to allow the peristaltic pump to deliver medical fluid at a controlled rate to a patient, and
   wherein an enabling means on said second receiving member switches said switch means from said second state to said first state to enable operation of said rotary member on said peristaltic pump when said magnetic field source is detected by said enabling means.

6. A fluid delivery apparatus for the delivery of a medical fluid to a patient, comprising
   a peristaltic pump having a rotary member and first and second receivers thereon,
   a switch means on said peristaltic pump for enabling the operation of said rotary member in a first state and disabling operation of said rotary member in a second state and wherein said switch means is normally in the second state,
   said second receiver having a magnetic field sensitive sensor adjacent thereto in operative communication with said switch means,
   a fluid delivery set including first, second and third tubing sections, a drip chamber and a mounting member having a magnetic field source thereon wherein said first tubing section provides fluid flow communication between a fluid reservoir and said drip chamber and wherein said second tubing section provides fluid flow communication between said drip chamber and said mounting member and wherein said third tubing section provides fluid flow communication between said mounting member and a patient,
   said second tubing section being sufficiently flexible so as to be operatively aligned about said rotary member when said fluid delivery set is operatively mounted on said peristaltic pump,
   said drip chamber and said mounting member being spaced apart a predetermined distance on said fluid delivery set such that when said second tubing section is operatively aligned about said rotary member, said drip chamber is insertable into said first receiver and said mounting member is insertable into said second receiver, and
   wherein said magnetic field sensitive sensor activates said switch means from the second state to the first state in response to the detection of said magnetic field source in said second receiver to enable the operation of the rotary member to deliver fluid to a patient at a controlled rate.

7. A fluid delivery set for the delivery of a medical fluid to a patient at a flow rate controlled by a rotor of a peristaltic pump having a magnetic field sensor and first and second receiving members oriented for receiving portions of and mounting said fluid delivery set in a predetermined and operation activating alignment about the rotor of the peristaltic pump, the fluid delivery set comprising:

a flexible tubing section having the first and second ends and having sufficient flexibility to be adapted to be stretched in the predetermined alignment about the rotor of the peristaltic pump, a drip chamber in fluid communication with said first end of said tubing section, said drip chamber including a chamber section dimensioned and adapted to be removably mountable in the first receiving member when said tubing section is placed in the predetermined alignment about the rotor of the peristaltic pump, and a mounting member in fluid communication with said second end of said tubing section, said mounting member including a shoulder section and a magnetic field source dimensioned and adapted to be removably mountable in the second receiving member when said tubing section is placed in the predetermined alignment about the rotor of the peristaltic pump, said magnetic field source being positioned on said mounting member to be mountable in operational proximity to the magnetic field sensor of the peristaltic pump when said tubing section is in the predetermined alignment about the rotor of the peristaltic pump to thereby activate the operation of the peristaltic pump.

8. The fluid delivery set of claim 7 wherein said magnetic field source is toroidally shaped and substantially enclosed in the second receiving member of the peristaltic pump when said tubing section is placed in the predetermined alignment about the rotor of the peristaltic pump.

9. A fluid delivery set for the delivery of a medical fluid to a patient from a source of medical fluid at a flow rate controlled by a rotor of a peristaltic pump having a magnetic field sensor and first and second receiving members oriented for receiving portions of and mounting said fluid delivery set in a predetermined and operation-activating alignment about the rotor of the peristaltic pump, the fluid delivery set comprising:

a flexible first tubing section having first and second ends and having sufficient flexibility to be adapted to be stretched in the predetermined alignment about the rotor of the peristaltic pump, a second tubing section having first and second ends, said first end adapted to be placed in fluid communication with a source of medical fluid, a drip chamber having first and second ends, said first end in fluid communication with said second end of said second tubing section and said second end of the drip chamber in fluid communication with said first end of said first tubing section, said drip chamber dimensioned and adapted to be removably mountable in the first receiving members when said first tubing section is placed in the predetermined alignment about the rotor of the peristaltic pump, a mounting member in fluid communication with said second end of said first tubing section, said mounting member including a magnetic field source dimensioned and adapted to be removably mountable in the second receiving member when said first tubing section is placed in the predetermined alignment about the rotor of the peristaltic pump, said magnetic field source being positioned on said mounting member to be adapted to be in operational proximity to the magnetic field sensor of the peristaltic pump when said first tubing section is in the predetermined alignment about the rotor of the peristaltic pump to thereby activate the operation of the peristaltic pump, and a third tubing section having a first end in fluid communication with said mounting member and a second end adapted to deliver medical fluid to a patient.

* * * * *

REEXAMINATION CERTIFICATE (1720th)

United States Patent [19]
Pasqualucci et al.

[11] B1 4,913,703
[45] Certificate Issued Jun. 16, 1992

[54] SAFETY INTERLOCK SYSTEM FOR MEDICAL FLUID PUMPS

[76] Inventors: Joseph Pasqualucci; Frederick F. Schweitzer, both of Watertown, N.Y.

Reexamination Request:
No. 90/002,390, Jul. 18, 1991

Reexamination Certificate for:
Patent No.: 4,913,703
Issued: Apr. 3, 1990
Appl. No.: 103,432
Filed: Sep. 30, 1987

[51] Int. Cl.⁵ ............................................. A61M 1/00
[52] U.S. Cl. .................................... 604/153; 604/151
[56] References Cited

U.S. PATENT DOCUMENTS

| | | |
|---|---|---|
| 3,935,876 | 2/1976 | Massie et al. |
| 4,080,967 | 3/1978 | O'Leary |
| 4,137,913 | 2/1979 | Georgi |
| 4,184,815 | 1/1980 | Casson et al. |
| 4,210,138 | 7/1980 | Jess et al. |
| 4,278,085 | 7/1981 | Shim |
| 4,312,341 | 1/1982 | Zissimopoulos et al. |
| 4,456,009 | 6/1984 | Vcelka et al. |
| 4,464,172 | 8/1984 | Lichtenstein |
| 4,519,792 | 5/1985 | Dawe |
| 4,540,964 | 9/1985 | Bleeke |
| 4,543,458 | 9/1985 | Holce et al. |
| 4,544,903 | 10/1985 | Grant |
| 4,557,725 | 12/1985 | Heyne et al. |
| 4,563,179 | 1/1986 | Sakai |
| 4,565,500 | 1/1986 | Jeensalute et al. |
| 4,568,254 | 2/1986 | Terada et al. |
| 4,585,441 | 4/1986 | Archibald |
| 4,610,658 | 9/1986 | Buchwald et al. |
| 4,636,144 | 1/1987 | Abe et al. |
| 4,638,278 | 1/1987 | Bullock |
| 4,650,469 | 3/1987 | Berg et al. |
| 4,652,260 | 3/1987 | Fenton, Jr. et al. |
| 4,661,093 | 4/1987 | Beck et al. |
| 4,668,216 | 5/1987 | Martin et al. |
| 4,673,389 | 6/1987 | Archibald et al. |
| 4,685,902 | 8/1987 | Edwards et al. |
| 4,695,271 | 9/1987 | Goethel |
| 4,714,463 | 12/1987 | Archibald et al. |
| 4,741,736 | 5/1988 | Brown |
| 4,752,289 | 6/1988 | Balding et al. |
| 4,755,109 | 7/1988 | Botts |
| 4,758,228 | 7/1988 | Williams |
| 4,798,589 | 1/1989 | Tseo |
| 4,808,089 | 2/1989 | Buchholtz et al. |
| 4,838,860 | 6/1989 | Groshong et al. |

*Primary Examiner*—C. Fred Rosenbaum

[57] ABSTRACT

A medical fluid delivery set is provided with a magnetic field source in the region of its mounting to a fluid flow control apparatus. The flow control apparatus includes a magnetic field sensitive switching component which detects the proper placement of the delivery set on the flow control apparatus and prevents operation of the fluid delivery system unless a set is in proper position.

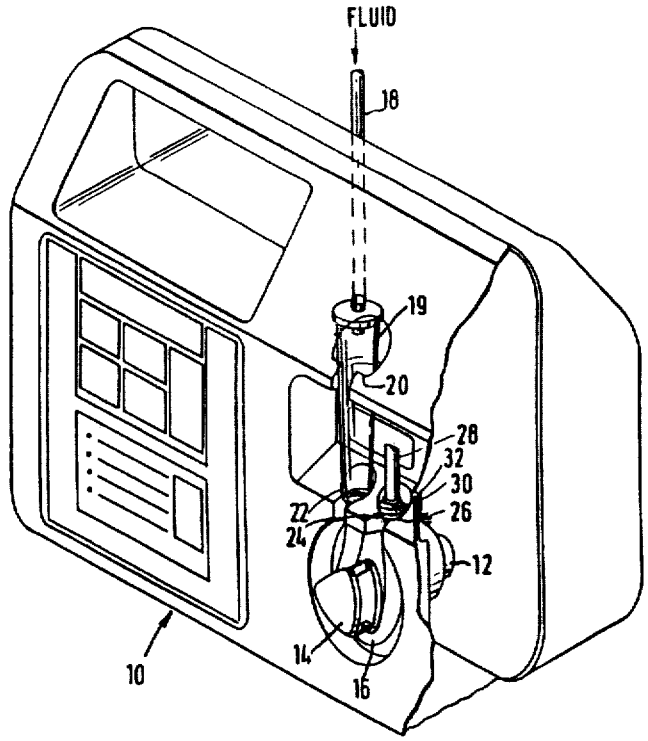

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-9 is confirmed.

* * * * *